(12) United States Patent
Watanabe et al.

(10) Patent No.: US 11,618,726 B2
(45) Date of Patent: Apr. 4, 2023

(54) METHOD FOR PRODUCING DIOL

(71) Applicant: Nippon Shokubai Co., Ltd., Osaka (JP)

(72) Inventors: Akimasa Watanabe, Kanagawa (JP); Akiko Yamauchi, Kanagawa (JP)

(73) Assignee: NIPPON SHOKUBAI CO., LTD., Osaka (JP)

(*) Notice: Subject to any disclaimer, the term of this patent is extended or adjusted under 35 U.S.C. 154(b) by 0 days.

(21) Appl. No.: 17/527,705

(22) Filed: Nov. 16, 2021

(65) Prior Publication Data
US 2022/0153667 A1    May 19, 2022

(30) Foreign Application Priority Data
Nov. 16, 2020 (JP) .............................. JP2020-190329

(51) Int. Cl.
*C07C 29/52* (2006.01)
*B01D 3/14* (2006.01)
(Continued)

(52) U.S. Cl.
CPC ............... *C07C 29/52* (2013.01); *B01D 3/12* (2013.01); *B01D 3/146* (2013.01); *C07C 29/80* (2013.01)

(58) Field of Classification Search
CPC ... C07C 29/80; C07C 31/276; C07C 2601/14; C07C 29/52; C07C 31/20; C07C 29/12; B01D 3/12; B01D 3/146
See application file for complete search history.

(56) References Cited

U.S. PATENT DOCUMENTS

| 4,515,775 A | 5/1985 | Vanlerberghe et al. |
| 7,211,701 B2 | 5/2007 | Muller et al. |

(Continued)

FOREIGN PATENT DOCUMENTS

| JP | S48-34571 A | 5/1973 |
| JP | S48-34807 A | 5/1973 |

(Continued)

OTHER PUBLICATIONS

JPO, Office Action for the corresponding Japanese patent application No. 2020-190329, dated Apr. 13, 2021, with English translation.

*Primary Examiner* — Jafar F Parsa
(74) *Attorney, Agent, or Firm* — Lucas & Mercanti, LLP

(57) ABSTRACT

[Objective] An object is to provide a method for producing a diol by which diols having a favorable color scale and containing a reduced amount of an unsaturated aliphatic hydrocarbon can be produced.
[Solution] A method for producing a diol, including a) supplying metaboric acid, a saturated aliphatic hydrocarbon and a reaction gas containing molecular oxygen to a reactor and performing liquid-phase oxidation of the saturated aliphatic hydrocarbon with the reaction gas containing molecular oxygen in the presence of metaboric acid to obtain a reaction liquid containing an oxide, b) esterifying the oxide to obtain a reaction liquid containing a borate compound, c) separating the reaction liquid containing a borate compound into an unreacted saturated aliphatic hydrocarbon and a distillation residue by distillation, d) separating the distillation residue into orthoboric acid and an organic layer by hydrolysis, e) separating the organic layer into an alkali aqueous solution layer and a crude alcohol layer by saponification with an alkali, and f) performing first distillation on the crude alcohol layer to remove a monoalcohol, and then performing second distillation on the residual liquid under (Continued)

conditions of a temperature of lower than 250° C. and a residence time of shorter than 60 minutes.

8 Claims, 1 Drawing Sheet

(51) Int. Cl.
  *B01D 3/12* (2006.01)
  *C07C 29/80* (2006.01)

(56) References Cited

U.S. PATENT DOCUMENTS

| | | | |
|---|---|---|---|
| 8,466,323 B2 | 6/2013 | Melder et al. | |
| 2003/0139631 A1 | 7/2003 | Muller et al. | |
| 2010/0267997 A1* | 10/2010 | Miller | C07C 29/80 |
| | | | 568/831 |
| 2011/0257437 A1 | 10/2011 | Melder et al. | |

FOREIGN PATENT DOCUMENTS

| | | |
|---|---|---|
| JP | S56-131531 A | 10/1981 |
| JP | S61-293508 A | 12/1986 |
| JP | H03-121116 A | 5/1991 |
| JP | 2003-192620 A | 7/2003 |
| JP | 2012-512826 A | 6/2012 |

\* cited by examiner

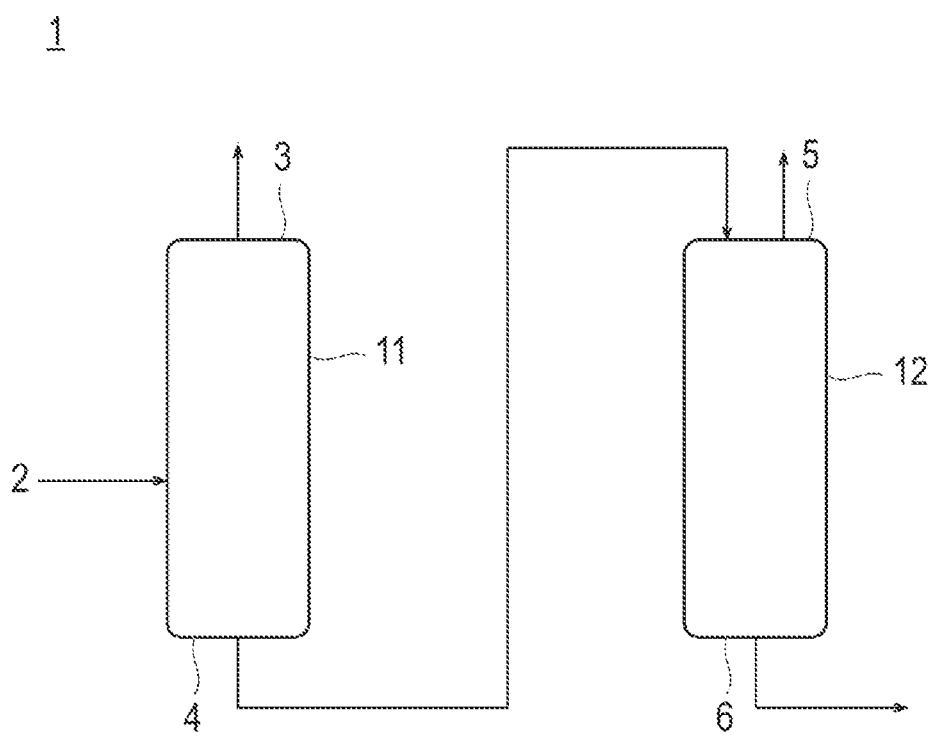

METHOD FOR PRODUCING DIOL

TECHNOLOGICAL FIELD

The present invention relates to a method for producing a diol.

BACKGROUND ART

Secondary alcohols are useful as a raw material for synthetic detergents, surfactants, plasticizers and the like. A technique enabling secondary alcohols to be obtained by performing an oxidation reaction step of introducing a reaction gas containing molecular oxygen in the presence of metaboric acid and a saturated aliphatic hydrocarbon to obtain a borate compound and then performing a hydrolysis step and a saponification step is known (for example, Japanese Patent Laid-Open No. 56-131531).

Incidentally, it is known that diols of secondary alcohols are also useful in use as an additive for surfactants, and it is also known that diols of secondary alcohols can be obtained by distillation of an alcohol mixture obtained in the production steps of a secondary alcohol (Japanese Patent Laid-Open No. 48-34807).

PRIOR ART REFERENCES

Patent Literatures

[Patent Literature 1] JP S56-131531 A
[Patent Literature 2] JP S48-34807 A

SUMMARY

Problem to be Solved by Invention

However, it was found that diols produced by the related art have a poor color scale or contain a large amount of an unsaturated aliphatic hydrocarbon.

Therefore, an object of the present invention is to provide a method for producing a diol by which diols having a favorable color scale and containing a reduced amount of an unsaturated aliphatic hydrocarbon can be produced.

Solution to Problem

An embodiment for achieving the above-described object is a method for producing a diol, including a) supplying metaboric acid, a saturated aliphatic hydrocarbon and a reaction gas containing molecular oxygen to a reactor and subjecting the saturated aliphatic hydrocarbon to liquid-phase oxidation with the reaction gas containing molecular oxygen in the presence of metaboric acid to obtain a reaction liquid containing an oxide, b) esterifying the oxide to obtain a reaction liquid containing a borate compound, c) distilling the reaction liquid containing a borate compound to separate the reaction liquid into an unreacted saturated aliphatic hydrocarbon and a distillation residue, d) hydrolyzing the distillation residue to separate it into orthoboric acid and an organic layer, e) subjecting the organic layer to saponification with an alkali to separate into an alkali aqueous solution layer and a crude alcohol layer, and f) performing first distillation on the crude alcohol layer to remove a monoalcohol therefrom and obtain a residual liquid, and then performing second distillation on the residual liquid under conditions of a temperature of lower than 250° C. and a residence time of shorter than 60 minutes.

Effects of Invention

According to the present invention, it is possible to provide a method for producing a diol by which diols having a favorable color scale and containing a reduced amount of an unsaturated aliphatic hydrocarbon can be produced.

BRIEF DESCRIPTION OF THE DRAWING

FIG. 1 is a schematic view in a step (f) of the present invention.

DETAILED DESCRIPTION OF EMBODIMENTS

Hereinafter, the present invention will be described. The present invention is not limited only to the following embodiment. In addition, unless particularly otherwise described, operations and measurement of physical properties and the like are conducted under a room temperature (20° C. to 25° C.) condition.

An embodiment in the present invention is a method for producing a diol, including a) supplying metaboric acid, a saturated aliphatic hydrocarbon and a reaction gas containing molecular oxygen to a reactor and performing liquid-phase oxidation of the saturated aliphatic hydrocarbon with the reaction gas containing molecular oxygen in the presence of metaboric acid to obtain a reaction liquid containing an oxide, b) esterifying the oxide to obtain a reaction liquid containing a borate compound, c) separating the reaction liquid containing a borate compound into an unreacted saturated aliphatic hydrocarbon and a distillation residue by distillation, d) separating the distillation residue into orthoboric acid and an organic layer by hydrolysis, e) separating the organic layer into an alkali aqueous solution layer and a crude alcohol layer by saponification with an alkali, and f) performing first distillation on the crude alcohol layer to remove a monoalcohol, and then performing second distillation on the residual liquid under conditions of a temperature of lower than 250° C. and a residence time of shorter than 60 minutes. According to such an embodiment, it is possible to provide a method for producing a diol by which diols having a favorable color scale and containing a reduced amount of an unsaturated aliphatic hydrocarbon can be produced.

Hereinafter, each step will be described in detail.
(Step (a))
(Step (a): Oxidation Reaction Step)

In a step (a), metaboric acid, a saturated aliphatic hydrocarbon and a reaction gas containing molecular oxygen (in the present specification, also simply referred to as "oxygen") is supplied to a reactor and liquid-phase oxidation of the saturated aliphatic hydrocarbon is performed with the reaction gas containing molecular oxygen in the presence of metaboric acid, thereby obtaining a reaction liquid containing an oxide.

The saturated aliphatic hydrocarbon is a mixture of saturated aliphatic hydrocarbons having 8 to 30 carbon atoms (normal paraffin). The saturated aliphatic hydrocarbon is preferably a mixture containing saturated aliphatic hydrocarbon having 10 to 15 carbon atoms (n-decane, n-undecane, n-dodecane, n-tridecane, n-tetradecane and n-pentadecane) as main components and more preferably a mixture containing saturated aliphatic hydrocarbons having 12 to 14 carbon atoms (n-dodecane, n-tridecane and n-tetradecane) as main components. Here, the expression "containing saturated aliphatic hydrocarbons as main components" means that the mixture contains saturated aliphatic hydrocarbons having a predetermined number of carbon atoms in a ratio of more than 90% by mass (preferably 95% by mass) (upper limit: 100% by mass) with respect to all of the saturated aliphatic hydrocarbons. In addition, the average molecular weight of the saturated aliphatic hydrocarbons is 114 or more and 422 or less, preferably 142 or more and 212 or less and more preferably 170 or more and 198 or less. The saturated aliphatic hydrocarbon may be synthesized or may be a commercially available product. Similarly, the metaboric acid also may be synthesized or may be a commercially available product.

In the step (a), the molecular oxygen-containing gas contains a nitrogen gas in addition to molecular oxygen (oxygen). The molecular oxygen-containing gas is preferably composed of molecular oxygen (oxygen) and a nitrogen gas. In addition, the concentration of the molecular oxygen (oxygen) in the molecular oxygen-containing gas is 1% by volume (vol %) or higher and 10% by volume (vol %) or lower and preferably 3% by volume (vol %) or higher and 5% by volume (vol %) or lower or the like, but is not limited thereto. The amount of the molecular oxygen-containing gas supplied is 100 to 1000 liters/hour and preferably 350 to 600 liters/hour or the like per 1000 g of the saturated aliphatic hydrocarbon, but is not limited thereto.

In the step (a), the reaction mixing ratio between the metaboric acid and the saturated aliphatic hydrocarbon is not particularly limited, but the amount of the metaboric acid is preferably 1% by mass or more and 5% by mass or less and more preferably 2% by mass or more and 4% by mass or less or the like of the saturated aliphatic hydrocarbon, but is not limited thereto.

The liquid-phase oxidation reaction conditions are not particularly limited, and the same conditions as in the related art can be applied in the same manner. For example, the liquid-phase oxidation reaction temperature is 100° C. to 250° C. and preferably 140° C. to 200° C. or the like, but is not limited thereto. In addition, the liquid-phase oxidation reaction time is, for example, 0.5 to 5 hours and preferably 1 to 3 hours or the like, but is not limited thereto. Under such conditions, liquid-phase oxidation of the saturated aliphatic hydrocarbon to an appropriate extent (for example, the conversion rate of the saturated aliphatic hydrocarbon=5% to 30%) with the molecular oxygen-containing gas is possible. The liquid-phase oxidation reaction may be performed under the atmospheric pressure (normal pressure), under increased pressure or under reduced pressure, but is normally performed under the atmospheric pressure (normal pressure) to 30 kg/cm$^2$G (3 MPa). In addition, the liquid-phase oxidation reaction may be performed under stirring (the reactor may include a stirrer).

In the step (a), the liquid-phase oxidation reaction may be performed in one reactor or may be performed in a plurality of (two or more) reactors in series. In addition, the reactor may be, for example, a stirring tank-type reactor or a bubble tower-type reactor.

(Step (b): Esterification Step)

In a step (b), the oxide (oxidation reaction product) is esterified to obtain a reaction liquid containing a borate compound.

In the step (b), a borate compound is generated; however, additionally, an unreacted aliphatic hydrocarbon, a free alcohol and metaboric acid are present. The free alcohol and the unreacted saturated aliphatic hydrocarbon have similar boiling points, which makes it difficult to separate both. Therefore, in the esterification step (b), this alcohol is converted into a borate compound by orthoborate esterification.

That is, in the step (b), the free alcohol that is contained in the oxidation reaction product obtained in the step (a) is esterified (orthoborate esterification) to obtain a borate compound. In the step, the free alcohol that is present in the oxidation reaction product that is obtained in the step (a) is reacted with metaboric acid and converted into a borate compound. Normally, since there is an excess of metaboric acid in the oxidation reaction product, it is not necessary to newly add metaboric acid to the oxidation reaction product, but there is also a case where metaboric acid is newly added. A method for converting the free alcohol into a borate compound is also not particularly limited, but a decompression treatment is preferably performed on the reaction liquid containing an oxide obtained in the step (a). In such a case, the free alcohol can be esterified with metaboric acid which had been excessively added (or newly-added metaboric acid) to give a borate compound. Conditions for this esterification are not particularly limited. In one embodiment of the present invention, in one embodiment of the present invention, the pressure in the step (b) is, for example, 50 to 200 hPa and preferably 90 to 170 hPa or the like. In the present specification, the pressure in the esterification step means the value of a pressure that is measured with a pressure meter installed in an upper portion of the reactor to measure the pressure of a gas-phase portion. The same definition will be similarly applied throughout the present specification. In one embodiment of the present invention, the temperature in the step (b) is, for example, 100° C. to 220° C. and preferably 160° C. to 180° C. or the like. In the present specification, the temperature in the esterification step means the value of a temperature that is measured with a thermometer inserted into a liquid in the reactor. The same definition will be similarly applied throughout the present specification. In one embodiment of the present invention, the treatment time in the step (b) is, for example, 5 to 80 minutes and preferably 20 to 60 minutes or the like. In the present specification, the treatment time in the reaction means the residence time in the reactor. Here, the residence time usually means a time for a substance that flows into a finite space to remain in the space. When the volume of the space is indicated by V (m$^3$) and the volume flow rate of the substance that flows into the space is indicated by θ (m$^3$/hr), the residence time (τ) is represented by the following equation.

$$\tau(hr) = V/\theta \qquad \text{[Math 1]}$$

In the step (a) and the step (b), the occurrence of the following reaction is included.

$$\text{ALIPHATIC HYDROCARBON (R)} \xrightarrow[\text{HBO}_2]{[O]}$$

$$\underbrace{\begin{array}{c} \text{OR} \\ | \\ \text{XO}^{\diagup}\text{B}^{\diagdown}\text{OX} \\ \\ X = R \text{ or } H \\ \text{BORIC ESTER} \end{array} + \begin{array}{c} \text{OR} \\ | \\ \text{O}^{\diagup}\text{B}^{\diagdown}\text{O} \\ | \quad \quad | \\ \text{XO}^{\diagup}\text{B}^{\diagdown}\text{O}^{\diagup}\text{B}^{\diagdown}\text{OX} \\ \\ X = R \text{ or } H \\ \text{BOROXINE} \end{array}}_{\text{BORATE COMPOUND}} + \text{WATER}$$

(Step (c): Recovery Step of Unreacted Saturated Aliphatic Hydrocarbon)

In a step (c), the reaction liquid containing a borate compound obtained in the step (b) is distilled to separate the reaction liquid into an unreacted saturated aliphatic hydrocarbon and a distillation residue (bottom residue liquid), and the unreacted saturated aliphatic hydrocarbon is recovered (unreacted saturated aliphatic hydrocarbon recovery step). Since there is a huge difference in boiling point between the distillate and the bottom residue liquid, the distillate and the bottom residue liquid can be easily separated from each other by distillation.

In the present step, as a method for distilling the borate compound, a known method such as simple distillation (for example, flash distillation) or molecular distillation can be used, but the method for distilling the borate compound is not limited thereto. Such distillation may be performed in one stage or may be performed in two or more stages.

In one embodiment of the present invention, the pressure in the step (c) is, for example, 1 to 50 hPa or 3 to 25 hPa. In the present specification, the pressure in the distillation means the value of a pressure that is measured with a pressure meter installed at the top to measure the pressure of the gas-phase portion. The same definition will be similarly applied throughout the present specification. In one embodiment of the present invention, the temperature in the step (c) is, for example, 130° C. to 250° C. or 150° C. to 205° C. In the present specification, the temperature in the distillation means the value of a temperature that is measured with a thermometer inserted into the liquid at the bottom. In one embodiment of the present invention, the residence time in the step (c) is, for example, 1 to 205 minutes or 25 to 120 minutes. Here, in the present specification, the residence time in the distillation means a value calculated by dividing the amount of the liquid retained in the distillation tower (the volume of the liquid) ($m^3$) by the amount of the liquid discharged from the bottom of the distillation tower ($m^3$/minute). Here, the amount of the liquid retained in the distillation tower is previously set such that the liquid at the bottom reaches a certain volume. The same definition will be similarly applied throughout the present specification.

The unreacted saturated aliphatic hydrocarbon recovered in the present step may be reused (circulated) in the oxidation reaction step (a). In this case, for example, the unreacted saturated aliphatic hydrocarbon itself removed from the distillate may be reused in the oxidation reaction step (a); the unreacted saturated aliphatic hydrocarbon may be reused in the oxidation reaction step (a) after a carbonyl compound and olefins that are contained in the saturated aliphatic hydrocarbon recovered in the present step are hydrogenated; or the unreacted saturated aliphatic hydrocarbon may be reused in the oxidation reaction step (a) as described in, for example, Japanese Patent Laid-Open No. 56-131531, after the saturated aliphatic hydrocarbon recovered in the present step is brought into contact with, for example, an alkali aqueous solution and separated into an organic layer containing an aliphatic acid and an aliphatic acid ester and a water layer, the organic layer is washed with hot water as necessary (alkali treatment step), an unreacted unsaturated aliphatic hydrocarbon that is contained in the organic layer is hydrotreated (hydrogen treatment step), and an alcohol component that is contained in the unreacted saturated aliphatic hydrocarbon is then converted into an orthoborate ester (esterification step), but not limited thereto.

(Step (d): Hydrolysis Step)

In a step (d), the distillation residue separated in the step (c) is separated into orthoboric acid and an organic layer by hydrolysis.

Specifically, the distillation residue is hydrolyzed by adding hot water thereto and separated into a water layer containing orthoboric acid and an organic layer. Here, the temperature of the hot water (liquid temperature) is 70° C. to 150° C. and preferably 90° C. to 100° C. or the like, but is not limited thereto. In addition, the amount of the hot water added is 1 to 20 times the mass and preferably 2 to 10 times the mass or the like of the distillation residue, but is not limited thereto. The hydrolysis time is 5 to 60 minutes and preferably 20 to 30 minutes or the like, but is not limited thereto. Under such conditions, the distillation residue can be sufficiently hydrolyzed and more efficiently separated into a water layer containing orthoboric acid and an organic layer.

(Step (e): Saponification Step)

In a step (e), the organic layer separated in the step (d) is separated into an alkali aqueous solution layer and a crude alcohol layer by a saponification treatment with an alkali (saponification step). This makes it possible to remove an organic acid or an organic acid ester.

Here, as the alkali, for example, sodium hydroxide, potassium hydroxide, sodium hydrogen carbonate, potassium hydrogen carbonate or the like can be used, but the alkali is not limited thereto. In addition, the layers may be washed with water as necessary after the saponification treatment with the alkali. The saponification conditions are not particularly limited, and the same conditions as in the related art can be applied in the same manner. For example, the saponification temperature is 120° C. to 160° C. and preferably 135° C. to 145° C. or the like, but is not limited thereto. The saponification time is 30 to 120 minutes and preferably 50 to 90 minutes or the like, but is not limited thereto. Under such conditions, the saponification treatment can be more efficiently progressed. After the saponification treatment, the organic layer may be washed with water in order to remove an organic acid or an organic acid ester.

(Step (f): Alcohol Purification Step)

In a step (f), first distillation is performed on the crude alcohol layer to remove a monoalcohol, and then second distillation is performed on the residual liquid under conditions of lower than 250° C. and a residence time of shorter than 60 minutes. This makes it possible to obtain a secondary alcohol and a diol having a favorable color scale and containing a reduced amount of an unsaturated aliphatic hydrocarbon.

FIG. 1 is a schematic view in the step (f) of the present invention. As shown in FIG. 1, a crude alcohol layer (organic layer) 2 left after the removal of the alkali aqueous solution layer in the step (e) is introduced into a first distiller 11. After that, the first distillation is performed. In one embodiment of the present invention, the pressure in the first distillation is, for example, 1 to 45 hPa, for example, 2 to 30 hPa, or, for example, 4 to 12 hPa.

Under such conditions, the crude alcohol layer 2 can be appropriately separated depending on boiling point ranges (into, for example, a fraction having a boiling point range of 95° C. or higher and lower than 120° C. and a fraction having a boiling point range of 120° C. to 150° C.), and these fractions are distilled from a top 3. At this time, a first fraction (the fraction having a boiling point range of 95° C. or higher and lower than 120° C.) is a mixture of a small amount of a saturated aliphatic hydrocarbon, a carbonyl compound and a monovalent primary alcohol (monoalcohol). In addition, a second fraction (the fraction having a boiling point range of 120° C. to 150° C.) is a mixture of a small amount of a carbonyl compound and a secondary alcohol (monoalcohol).

Next, a liquid of a residue at a bottom 4 after the removal of the monoalcohol in the first distillation by rectification is introduced into a second distiller 12. The second distillation is performed using this liquid as a raw material liquid. In one embodiment of the present invention, the raw material liquid contains 70% to 98% by mass, 80% to 97% by mass or 85% to 95% by mass of a crude diol. In one embodiment of the present invention, the raw material liquid contains 0.1% to 10% by mass, 0.5% to 7% by mass or 1% to 5% by mass of an alkali component. Even when an alkali component is contained to a certain extent as in such an embodiment, there is no adverse influence on the quality of the diol, and thus there is no disadvantage. In other words, there is no need of a step such as water washing before the distillation, and an alkali may be present. Therefore, in one embodiment of the present invention, no water washing step is included between the first distillation and the second distillation in order to reduce or remove the alkali. In such an embodiment, improvement in productivity can be expected. In one embodiment of the present invention, the raw material liquid contains 1% to 20% by mass, 2% to 18% by mass, 2.5% to 13% by mass or 4% to 10% by mass of a heavy oil component. In one embodiment of the present invention, the total of the crude diol, the alkali component and the heavy oil component is 100% by mass. Examples of the heavy oil component include triols, tetraols and organic acid salts.

In one embodiment of the present invention, the temperature in the second distillation is 240° C. or lower, 230° C. or lower, 220° C. or lower, lower than 220° C., 210° C. or lower, 205° C. or lower, lower than 205° C., 200° C. or lower, 190° C. or lower, 180° C. or lower, 175° C. or lower, 170° C. or lower or 165° C. or lower. In one embodiment of the present invention, the temperature in the second distillation is 150° C. or higher, 160° C. or higher, 170° C. or higher, 180° C. or higher, 190° C. or higher, 200° C. or higher or 210° C. or higher.

In one embodiment of the present invention, the residence time in the second distillation (for example, distillation in which a simple distiller is used) is 50 minutes or shorter, 45 minutes or shorter, shorter than 45 minutes, 40 minutes or shorter, 35 minutes or shorter, 30 minutes or shorter, shorter than 30 minutes, 25 minutes or shorter or 20 minutes or shorter. In one embodiment of the present invention, the residence time in the second distillation (for example, distillation in which a simple distiller is used) is 10 minutes or longer, 20 minutes or longer, 25 minutes or longer, 30 minutes or longer or 45 minutes or longer.

In one embodiment of the present invention, the residence time in the second distillation (for example, distillation in which a molecular distiller is used) is 50 minutes or shorter, 45 minutes or shorter, shorter than 45 minutes, 40 minutes or shorter, 35 minutes or shorter, 30 minutes or shorter, shorter than 30 minutes, 25 minutes or shorter, 20 minutes or shorter, 15 minutes or shorter, shorter than 15 minutes, 10 minutes or shorter, 8 minutes or shorter, 6 minutes or shorter or 4 minutes or shorter. In one embodiment of the present invention, the residence time in the second distillation (for example, distillation in which a molecular distiller is used) is 0.5 minutes or longer, 1 minute or longer, 2 minutes or longer, 5 minutes or longer, 10 minutes or longer, 20 minutes or longer, 25 minutes or longer, 30 minutes or longer or 45 minutes or longer.

In one embodiment of the present invention, the pressure in the second distillation is 4 to 20 hPa, 5 to 18 hPa, 5 to 14 hPa, 5 to 12 hPa, 5 to 10 hPa, or 6 to 8 hPa.

In one embodiment of the present invention, the second distillation is performed by simple distillation, the temperature is lower than 200° C., and the residence time is shorter than 45 minutes.

In one embodiment of the present invention, the second distillation is performed by molecular distillation, the temperature is lower than 220° C., and the residence time is shorter than 45 minutes. In such an embodiment, the temperature is lower than 205° C. In such an embodiment, the residence time is shorter than 30 minutes. In such an embodiment, the residence time is shorter than 15 minutes.

According to one embodiment of the present invention, a method for producing a diol, including a) supplying metaboric acid, a saturated aliphatic hydrocarbon and a reaction gas containing molecular oxygen to a reactor and performing liquid-phase oxidation of the saturated aliphatic hydrocarbon with the reaction gas containing molecular oxygen in the presence of metaboric acid to obtain a reaction liquid containing an oxide, b) esterifying the oxide to obtain a reaction liquid containing a borate compound, c) separating the reaction liquid containing a borate compound into an unreacted saturated aliphatic hydrocarbon and a distillation residue by distillation, d) separating the distillation residue into orthoboric acid and an organic layer by hydrolysis, e) separating the organic layer into an alkali aqueous solution layer and a crude alcohol layer by saponification with an alkali, and f) performing first distillation on the crude alcohol layer to remove a monoalcohol, and then performing second distillation on the residual liquid under a condition of a predetermined thermal load parameter or less is also provided. Here, the predetermined thermal load parameter can be calculated by the product of the temperature (° C.) in the distillation and the residence time (minutes).

In one embodiment of the present invention, in a case where the second distillation is performed using a simple distiller, the thermal load parameter is 9000 or less, 8000 or less, 7000 or less, 6000 or less, 5000 or less or 4000 or less. In one embodiment of the present invention, in a case where the second distillation is performed using a simple distiller, the thermal load parameter is 1000 or more, 2000 or more, 2500 or more or 3000 or more.

In one embodiment of the present invention, in a case where the second distillation is performed using a molecular distiller, the thermal load parameter is 9000 or less, 8000 or less, 7000 or less, 6000 or less, 5000 or less, 4000 or less, 3000 or less, 2000 or less, 1000 or less, 900 or less, 800 or less or 700 or less. In one embodiment of the present invention, in a case where the second distillation is performed using a molecular distiller, the thermal load parameter is 100 or more, 200 or more, 300 or more, 400 or more, 500 or more, 600 or more, 800 or more, 2000 or more, 2500 or more or 3000 or more.

In one embodiment of the present invention, as a method for each of the first distillation and the second distillation in the step (f), a known method such as simple distillation (for example, flash distillation) or molecular distillation can be used independently, but the method for each of the first distillation and the second distillation is not limited thereto.

In one embodiment of the present invention, a simple distillation device is composed of an evaporator, a condenser, a distillate receiver, a liquid feeding pump and the like.

In one embodiment of the present invention, in the step (f), the first distillation is performed by simple distillation (for example, flash distillation), and the second distillation is performed by simple distillation (for example, flash distillation). Such an embodiment makes the intended effect of the present invention efficiently exhibited.

In one embodiment of the present invention, in the step (f), the first distillation is performed by simple distillation (for example, flash distillation), and the second distillation is performed by molecular distillation. Such an embodiment makes the intended effect of the present invention more efficiently exhibited.

In one embodiment of the present invention, the color scale of a diol that is the object (a diol of a secondary alcohol) is preferably less than 100, 90 or less, 80 or less, 70 or less or 60 or less. In one embodiment of the present invention, the color scale of the diol that is the object (a diol of a secondary alcohol) is, for example, 40 or more or 45 or more. Here, in the present specification, the value of the color scale is calculated by comparison with the color scale of the APHA standard solution, specifically, a method based on JIS K 0071: 2017. The color scales are also calculated using this method in examples.

In one embodiment of the present invention, the iodine value of the diol that is the object (a diol of a secondary alcohol) is preferably less than 17, 16 or less, 15 or less, 13 or less or 12 or less. In one embodiment of the present invention, the iodine value of the diol that is the object (a diol of a secondary alcohol) is, for example, 8 or more or 10 or more. Here, the iodine value is measured by a Wijs method (JIS K 0070: 1992). The iodine values are also measured using this method in examples. When the iodine value is high, it is possible to determine that there is a large amount of the unsaturated aliphatic hydrocarbon. The unsaturated aliphatic hydrocarbon is an impurity and is considered to adversely affect the color scale and thus leads to the deterioration of the quality.

According to known conventional methods, at least one step selected from a heavy oil separation step, an alkali treatment step (particularly, a potassium hydroxide treatment step) and a light oil separation step may be performed between the step (e) and the present step (f).

EXAMPLES

Hereinafter, the present invention will be more specifically described with examples and comparative examples, but the present invention is not interpreted to be limited to these examples and comparative examples, and examples that are obtained by appropriately combining technical means disclosed in the individual examples are also included in the scope of the present invention.

Examples 1 to 9 and Comparative Example 1

A mixture of saturated aliphatic hydrocarbons having 12 to 14 carbon atoms (1000 g) and metaboric acid (25 g) were fed into a cylindrical reactor having a capacity of 3 L, a gas mixture having an oxygen concentration of 3.5 vol % and a nitrogen concentration of 96.5 vol % was blown into the reactor in a ratio of 430 L per hour, and an oxidation reaction was performed at normal pressure and 170° C. for two hours, thereby obtaining an oxidation reaction liquid mixture (oxide) (oxidation reaction step). The mixture of saturated aliphatic hydrocarbons had an average molecular weight of 184 and contained saturated aliphatic hydrocarbons having 12 to 14 carbon atoms (n-dodecane, n-tridecane and n-tetradecane) in a ratio of more than 95% by mass with respect to the total mass of the mixture.

After the oxidation reaction, a reaction liquid containing the oxide was decompressed and thereby esterified with an alcohol and excessively-added boric acid, thereby obtaining a borate compound. This esterification was performed at 105 hPa and 165° C. for 60 minutes (esterification step).

Next, flash distillation was performed on this borate compound (boric acid ester mixture) at 200° C. and 7 hPa, thereby removing an unreacted saturated aliphatic hydrocarbon (unreacted saturated aliphatic hydrocarbon recovery step).

Next, a residue liquid was hydrolyzed with a large amount (an amount twice the mass of the residue liquid) of hot water (95° C.) for 25 minutes and separated into a water layer containing orthoboric acid and an organic layer (hydrolysis step).

The obtained organic layer was saponified at 140° C. for 80 minutes using sodium hydroxide and washed with water, thereby removing an organic acid and an organic acid ester (alkali aqueous solution layer) (saponification step).

As shown in FIG. 1, a crude alcohol layer (organic layer) 2 left after the removal of the alkali aqueous solution layer in the saponification step was introduced into a first distiller (simple distiller) 11 and fractionally distilled at 7 hPa, thereby obtaining a fraction having a boiling point range of 95° C. or higher and lower than 120° C. as a first fraction and a fraction having a boiling point range of 120° C. to 150° C. as a second fraction from a top 3. Here, the first fraction (fraction of 95° C. or higher and lower than 120° C.) was a mixture of a small amount of a saturated aliphatic hydrocarbon, a carbonyl compound and a monovalent primary alcohol (monoalcohol). The second fraction (fraction having a boiling point range of 120° C. to 150° C.) was a mixture of a small amount of a carbonyl compound and a secondary alcohol (monoalcohol), and, at this time, the majority of the secondary alcohol was a monovalent secondary alcohol. First distillation was performed as described above.

Next, a liquid of a residue at a bottom 4 after the removal of the monoalcohol in the first distillation by rectification was introduced into a second distiller (simple distiller) 12, and second distillation was performed using this liquid as a raw material liquid at a temperature and a pressure for a residence time shown in Table 1 below. The raw material liquid was composed of 90% by mass of a crude diol, 2% by mass of an alkali component and 8% by mass of a heavy oil component (triol, tetraol or organic acid salt).

TABLE 1

| | Second distiller (simple distillation tower) | | | | |
|---|---|---|---|---|---|
| | Temperature ° C. | Pressure hPa | Residence time Min. | Color scale APHA | Iodine value (IV) |
| Example 1 | 200 | 7 | 30 | 80 | 15 |
| Example 2 | 195 | 7 | 30 | 70 | 14 |
| Example 3 | 185 | 7 | 30 | 70 | 13 |
| Example 4 | 170 | 7 | 30 | 70 | 13 |
| Example 5 | 160 | 7 | 30 | 60 | 13 |
| Comparative Example 1 | 195 | 7 | 60 | 100 | 17 |
| Example 6 | 195 | 7 | 45 | 80 | 15 |
| Example 7 | 195 | 7 | 20 | 60 | 13 |
| Example 8 | 195 | 7 | 15 | 60 | 13 |
| Example 9 | 195 | 15 | 30 | 70 | 14 |

Examples 10 to 15 and Comparative Example 2

The same operations as in Example 1 were performed except that the second distiller (simple distiller) was changed to a second distiller (molecular distiller) and second distillation as performed at a temperature and a pressure for a residence time shown in Table 2 below.

TABLE 2

Second distiller (molecular distillation tower)

| | Temperature °C. | Pressure hPa | Residence time Min. | Color scale APHA | Iodine value (IV) |
|---|---|---|---|---|---|
| Comparative Example 2 | 250 | 7 | 3 | 100 | 16 |
| Example 10 | 220 | 7 | 3 | 80 | 15 |
| Example 11 | 205 | 7 | 3 | 70 | 14 |
| Example 12 | 195 | 7 | 3 | 50 | 12 |
| Example 13 | 185 | 7 | 3 | 50 | 12 |
| Example 14 | 170 | 7 | 3 | 50 | 12 |
| Example 15 | 195 | 15 | 3 | 50 | 12 |

As shown in Tables 1 and 2, it is suggested that the methods in the examples were a method for producing a diol by which diols having a favorable color scale and containing a reduced amount of an unsaturated aliphatic hydrocarbon can be produced.

REFERENCE SIGNS LIST

1 Distiller
11 First distiller
12 Second distiller
2 Crude alcohol layer left after removal of alkali aqueous solution layer in step (e) (organic layer)
3 Top of first distiller
4 Bottom of first distiller
5 Top of second distiller
6 Bottom of second distiller

The invention claimed is:

1. A method for producing a diol, comprising:
a) supplying metaboric acid, a saturated aliphatic hydrocarbon and a reaction gas containing molecular oxygen to a reactor and performing liquid-phase oxidation of the saturated aliphatic hydrocarbon with the reaction gas containing molecular oxygen in the presence of metaboric acid to obtain a reaction liquid containing an oxide;
b) esterifying the oxide to obtain a reaction liquid containing a borate compound;
c) separating the reaction liquid containing a borate compound into an unreacted saturated aliphatic hydrocarbon and a distillation residue by distillation;
d) separating the distillation residue into orthoboric acid and an organic layer by hydrolysis;
e) separating the organic layer into an alkali aqueous solution layer and a crude alcohol layer by saponification with an alkali; and
f) performing first distillation on the crude alcohol layer to remove a monoalcohol therefrom and obtain a residual liquid, and then performing second distillation on the residual liquid under conditions of a temperature of lower than 250° C. and a residence time of shorter than 60 minutes,
wherein the second distillation is performed by a simple distillation or a molecular distillation,
in a case where the second distillation is performed using the simple distiller, a thermal load parameter calculated by a product of the temperature in ° C. in the second distillation and the residence time in minutes is 5850 or less,
in a case where the second distillation is performed using the molecular distiller, the thermal load parameter calculated by the product of the temperature in ° C. in the second distillation and the residence time in minutes is 615 or less.

2. The method for producing a diol according to claim 1, wherein the temperature is lower than 220° C.

3. The method for producing a diol according to claim 1, wherein the residence time is shorter than 45 minutes.

4. The method for producing a diol according to claim 1, wherein the second distillation is performed by the simple distillation, and the temperature is 195° C. or lower, and residence time is 30 minutes or shorter.

5. The method for producing a diol according to claim 1, wherein the second distillation is performed by the molecular distillation, and the temperature is 205° C. or lower, and the residence time is 3 minutes or shorter.

6. The method for producing a diol according to claim 1, wherein the conditions include a pressure of 4 to 15 hPa.

7. The method for producing a diol according to claim 1, wherein the diol has a color scale of 70 or less.

8. The method for producing a diol according to claim 1, wherein the diol has an iodine value of 14 or less.

* * * * *